United States Patent [19]

Sones

[11] Patent Number: 4,709,382
[45] Date of Patent: Nov. 24, 1987

[54] IMAGING WITH FOCUSED CURVED RADIATION DETECTORS

[75] Inventor: Richard A. Sones, Cleveland Heights, Ohio

[73] Assignee: Picker International, Inc., Cleveland, Ohio

[21] Appl. No.: 673,779

[22] Filed: Nov. 21, 1984

[51] Int. Cl.$^4$ ............................................. G01T 1/161
[52] U.S. Cl. ......................................... 378/62; 378/5; 378/19; 378/146
[58] Field of Search ....................... 378/5, 19, 99, 146, 378/62

[56] References Cited

U.S. PATENT DOCUMENTS

| | | | |
|---|---|---|---|
| 3,965,358 | 6/1976 | Macovski | 378/5 |
| 4,015,129 | 3/1977 | Manring | 378/4 |
| 4,029,963 | 6/1977 | Alvarez et al. | 378/5 |
| 4,069,422 | 1/1978 | Hounsfield | 378/5 |
| 4,096,390 | 6/1978 | Hounsfield | 378/5 |
| 4,164,657 | 8/1979 | Duinker et al. | 378/19 |
| 4,176,279 | 11/1979 | Schwierz et al. | 378/4 |
| 4,176,280 | 11/1979 | Greschat et al. | 378/19 |
| 4,190,772 | 2/1980 | Dinwiddie et al. | 378/15 |
| 4,206,361 | 6/1980 | Hounsfield et al. | 378/19 |
| 4,247,774 | 1/1981 | Brooks | 378/19 |
| 4,295,047 | 10/1981 | Koga et al. | 250/363 S |
| 4,298,800 | 11/1981 | Goldman | 378/19 |
| 4,315,157 | 2/1982 | Barnes | 378/10 |
| 4,355,409 | 10/1982 | Amplatz | 378/146 |
| 4,366,574 | 12/1982 | Hill | 378/99 |
| 4,383,327 | 5/1983 | Kruger | 378/19 |
| 4,394,738 | 7/1983 | Wagner | 364/414 |
| 4,411,012 | 10/1983 | Pfeiler et al. | 378/17 |
| 4,426,721 | 1/1984 | Wang | 378/99 |
| 4,442,489 | 4/1984 | Wagner | 364/414 |
| 4,511,799 | 4/1985 | Bjorkholm | 378/99 |
| 4,626,688 | 12/1986 | Barnes | 250/361 R |

FOREIGN PATENT DOCUMENTS 0089148 9/1983 European Pat. Off. .
0115125 8/1984 European Pat. Off. .

OTHER PUBLICATIONS

Fenster, A., "Split Detector for Tomochemestry in Computed Tomography", *Jour. Comp. Assist Tomography*, 2:243-252, Jul. 1978.

B. A. Arnold, H. Eisenberg, D. Borger and A. Metherell, "Digital Radiography: An Overview", *Proceedings of SPIE*, vol. 273 *Application of Optical Instrumentation in Medicine* (Mar. 1981), pp. 215-226.

R. A. Mattson, R. A. Sones, J. B. Stickney, M. M. Tesic and G. T. Barnes, "The Design and Physical Characteristics of a Digital Chest Unit", SPIE, vol. 314, *Digital Radiography* (1981).

R. A. Kruger, C. A. Mistretta, J. Lancaster, T. L. Houk, M. Goodsitt, C. G. Shaw, S. J. Riederer, J. Hicks, J. Sackett, A. B. Crummy and D. Fleming, "A Digital Video Image Processor for Real-Time X-Ray Subtraction Imaging", *Optical Engineering*, vol. 17, No. 6 (Nov.-Dec. 1978), pp. 652-657.

*Primary Examiner*—Janice A. Howell
*Assistant Examiner*—Constantine Hannaher
*Attorney, Agent, or Firm*—Watts, Hoffman, Fisher & Heinke Co.

[57] ABSTRACT

A digital radiography system is disclosed having a multi-element curved detector assembly. The system includes an X-ray tube having a focal spot from which its X-ray energy primarily emanates, and which is spaced from the detector assembly to define a subject examination space. The detector assembly includes a number of individual detector elements each having a radiation sensitive face, the element faces collectively defining a concave curved surface oriented toward the focal spot. The assembly of elements can embody forms including a single curved line of elements, multiple similarly curved lines defining collectively a portion of a cylinder, or a three-dimensional curved array defining a portion of a sphere. Multiple layer stacked arrays can also be used. Each element responds to incident X-rays to produce an electrical charge signal indicative of the radiation. The detector assembly can be scanned relative to a subject in the examination space, and time delay and integrate circuitry is employed to improve the signal to noise characteristics of data represented by the electrical signals, by shifting and adding the signals in synchrony with scan motion prior to processing by imaging circuitry to derive a visual image of internal structure of a subject at the examination space.

35 Claims, 8 Drawing Figures

IMAGING WITH FOCUSED CURVED RADIATION DETECTORS

DESCRIPTION

1. Technical Field

This invention relates generally to the field of radiation imaging, and more particularly to medical diagnostic digital radiography employing focused curved arrays of individual radiation detector elements.

2. Background Art

Radiography is a long known medical diagnostic imaging technique.

In a conventional radiography system, an x-ray source is actuated to direct a divergent area beam of x-rays through a patient. A cassette containing an x-ray sensitive phosphor screen and light and x-ray sensitive film is positioned in the x-ray beam on the side of the patient opposite the source. X-radiation passing through the patient's body is thereby attenuated in various degrees to produce on the film a shadow image of a portion of the patient through which the x-rays pass.

More recently, digital radiographic techniques and systems have been developed. In digital radiography the source directs x-radiation through a patient's body to a detector assembly located in the beam path beyond the patient. The detector produces electrical signals defining the radiation pattern emergent from the patient and incident on the assembly. These signals are then processed to yield a visual display of the image.

The detector assembly includes an elongated planar array of individual detector elements. A detector element can suitably comprise a scintillator having a receiving face positioned in front of a photodiode. Each detector element responds to incident x-radiation to produce an analog electrical charge signal indicative of such radiation. These analog electrical signals represent the radiation pattern emergent from the patient's body.

The analog signals are sampled and processed by imaging circuitry, primarily to improve their signal to noise ratio, and are subsequently digitized.

The digital signals are fed to a digital data processing unit. The data processing unit records and/or processes and enhances the digital data.

A display unit responds to appropriate digital data representing the image to convert the digital information back into analog form and to produce a visual display of the patient's internal body structure derived from the acquired image pattern of radiation. The display unit can be coupled directly to the digital data processing unit for substantially real time imaging, or can be fed stored digital data from digital storage means such as tapes or disks, representing patient images produced from earlier studies.

Digital radiography includes techniques in which a thin spread beam of X-radiation is used. In practice of this technique, often called "scan (or slit) projection radiography" (SPR), the spread beam is scanned across the patient, or the patient is movably interposed between the spread beam x-ray source and the detector assembly, the detector being maintained in continuous alignment with the beam. The relative movement effected between the source-detector arrangement and the patient's body scans a large portion of the body.

Discrete element detectors have been proposed comprising a single line of detector elements. Other proposals have included planar rectangular detector arrays of square detector elements.

Details of certain aspects of digital radiography systems such as described here are set forth in the following publications, hereby expressly incorporated by reference:

Mattson, R. A., et al., "Design and Physical Characteristics of a Digital Chest Unit", S.P.I.E. Volume 314, *Digital Radiography* (1981);

Arnold, B. A. et al. "Digital Radiography: An overview" *Proceedings of S.P.I.E.* Volume 273, March 1981;

Kruger, R. A. et al. "A Digital Video Image Processor for Real Time x-ray Subtraction Imaging" *Optical Engineering,* Volume 17, No. 6 (1978);

U.S. Pat. No. 4,383,327, issued on May 10, 1983, to Kruger.

European Patent Application Publication No. EP 0115125-A1, published Aug. 8, 1984, by Gary L. Barnes and entitled "Spirit Energy Level Radiation Detection";

U.S. patent application Ser. No. 542,384, filed Oct. 17, 1983 by Mattson, R. A., et al. entitled "Improving Signal Characteristics in Digital Scan Projection Radiography", and owned by the assignee of this application, abandoned.

U.S. patent application Ser. No. 653,955, filed by Sones, et al. on Sept. 21, 1984, entitled "Digital Radiography Detector Resolution Improvement" and owned by the assignee of this application, abandoned.

It has also been proposed, where the detector array comprises a planar rectangular array of square detector elements, to improve the signal to noise ratio of the information developed by the detector, by the use of time delay and integrate (TDI) circuitry. An embodiment of such a proposed system is described in U.S. Pat. No. 4,383,327, issued on May 10, 1983 to Kruger, which is hereby incorporated by reference. Such proposed TDI systems employ sampling at regular intervals of detector motion, and motion-synchronous shifting and adding of the individual detector-produced analog charge signals which are sampled.

An important technique for enhancing a digitally represented image is called "subtraction". There are two types of subtraction techniques, one being "temporal" subtraction, the other being "energy" subtraction.

Temporal, sometimes called "mask mode" subtraction, is a technique that can be used to remove overlying and underlying structures from an image when the object of interest is enhanced by a radiopaque contrast agent. Images are acquired with and without the contrast agent present and the data representing the former image is subtracted from the data representing the latter, substantially cancelling out all but the blood vessels or anatomical regions containing the contrast agent.

A principal limitation of digital temporal subtraction is the susceptibility to misregistration, or "motion artifacts" caused by patient movement between the acquisition of the images with and without the contrast agent.

An alternative to temporal subtraction, which is less susceptible to motion artifacts, is energy subtraction. Whereas temporal subtraction depends on changes in the contrast distribution with time, energy subtraction exploits energy-related differences in attenuation properties of various types of tissues, such as the difference of the attenuation characteristics of soft tissue and bone.

Soft tissue shows less change in attenuation capability with respect to energy than does bone.

This phenomenon enables performance of energy subtraction. In practicing that technique, pulses of x-rays having alternating higher and lower energy levels are directed through the patient's body. When a lower energy pulse is so generated, the detector and associated digital processing unit cooperate to acquire and store a set of digital data representing the image produced in response to the lower energy pulse. A very short time later, when the higher energy pulse is produced, the detector and digital processing unit again similarly cooperate to acquire and store a separate set of digital information representing the image produced by the higher energy pulse. The values obtained representing the lower and higher energy images are then processed in accordance with techniques described in the following publication, hereby incorporated by reference: Lehman, L. A. et al., "Generalized Image Combination in Dual KVP Digital Radiography" *Medical Physics* Volume 8, pp. 659–667 (1981). By processing in this manner, the image contrast and visibility of different tissues is substantially enhanced.

Energy subtraction has the advantage, relative to temporal subtraction, of being substantially not subject to motion artifacts resulting from the patient's movement between exposures. The time separating the lower and higher imaging acquisitions is quite short, often less than one sixtieth of a second.

An important disadvantage in dual energy subtraction techniques results from the necessity of rapidly alternating the output of an x-ray tube between high and low levels. This requirement gives rise to severe problems in a practical clinical device. The switching frequency is required to be on the order of 500 Hz. and insufficient photons (x-ray energy) result when even the highest capacity x-ray tubes are combined with realistically narrow x-ray beam slit widths and rapid scanning rates.

In order to eliminate this problem, a detector assembly has been proposed which enables the practice of energy subtraction radiography with the use of a constant output x-ray source.

In accordance with this proposal, a dual layer planar dual energy radiation detector assembly has been suggested. A first layer comprises a rectangular planar array of square detector photodiode elements including a first radiation sensitive scintillation material overlying the photodiodes and being selected for its primary response to radiation of a lower energy range. A second planar layer is located, or "stacked", directly behind the first layer, with respect to the x-ray tube, and comprises a similar rectangular array of detector elements congruent and aligned with the first layer. The second layer includes a second radiation sensitive scintillation material selected for its propensity to respond primarily to radiation of a higher energy level, which has passed through the first layer substantially without being detected.

Such a dual energy detector structure, when used in conjunction with an x-ray tube emitting energy over a wide range, will provide data describing two separate images, i.e., one an image of lower energy x-radiation passing through the subject, the other being an image describing the pattern of higher energy radiation.

A flat rectangular detector of any type, however, has the inherent disadvantage that radiation intensity falling upon the various detector elements is a function of the element's relative position in the array, in addition to being a function of the patient's body structure. This results from the fact that x-ray energy traveling from the x-ray tube focal spot toward a detector element near the image periphery must travel a longer path when x-ray energy directed toward the central portion of the detector. This disadvantage is a problem in both single and dual energy flat detector systems.

With a flat detector, x-rays incident on centrally located detector elements enter the scintillator nearly normal to the receiving face. Rays incident on peipherally located elements enter the scintillators at angles which vary considerably from the normal. Under such conditions, a ray entering a peripheral element travels a longer path within its respective scintillator than does a ray entering central elements. Due to the longer paths traveled, a ray entering a peripheral element produces a greater scintillation than does a ray of equal value entering a central element, causing a response by the peripheral element that falsely exaggerates the indicated energy of the ray entering the peripheral element.

This problem acquires yet another aspect where a dual energy detector is used having two sets of "stacked" detector element arrays. A greater proportion of a ray's energy is dissipated in passage through a peripheral element than in passage through a central element. Therefore, a smaller fraction of energy incident on a peripheral front layer detector element is left to actuate a rear peripheral detector element than would be left to actuate a rear central detector after passage through a front central element. This phenonenon distorts the relative responses of the dual energy detector arrays, or layers, in a way which is very difficult to correct.

Where a flat dual energy detector, as described above, is used, there is an additional disadvantage. Due to parallax, image features viewed by the second detector layer, behind the first detector layer, will be seen as slightly spatially displaced with respect to the same image features as seen by the first detector layer. Therefore, the image produced by the second detector layer will differ slightly from that of the first, which difference will degrade the quality of the energy subtraction image which is derived when the first image data is subtracted from or combined with the second.

It is an object of this invention to provide a dual energy digital radiography system having a detector wherein the imaging response is uniform over the detector surface, and which does not suffer disadvantages of parallax.

DISCLOSURE OF INVENTION

The disadvantages of the prior art as described above are reduced or eliminated by the use of a digital radiographic system incorporating the present invention.

Such a digital radiographic system includes an x-ray source and a detector assembly maintained in a spaced relationship to define a subject examination space therebetween. The detector assembly includes a plurality of individual detector elements each having a radiation sensitive face. The radiation sensitive faces of the individual detector elements collectively generally define a concave curved surface oriented toward the x-ray tube. The system further includes operating power means for actuating the tube to propagate x-rays toward the detector and through the subject examination space. Imaging circuitry coupled to the detector elements processes data from the detector elements to form a representation of an image of internal structure of a subject when located at the subject examination space.

The curved surface collectively defined by the detector element faces increases uniformity of response of the detector with respect to element position by reducing differences in the lengths of the x-ray paths from the tube to the respective detector elements. The curved surface also substantially eliminates differences in the lengths of the x-ray paths in the detector itself, which also increases uniformity of response.

Where a dual energy, dual layer detector is used, the concavity of the detector configuration substantially eliminates any parallax effect which is typically suffered by flat split energy detector arrays.

Also, nonuniformity in the relative amounts of x-ray absorption in the front and back layers is substantially eliminated, making the dual energy technique much easier to implement.

In accordance with a more specific feature of the invention, the x-ray tube defines a focal spot or neighborhood from which most of its x-radiation emanates, and the detector concave curvature defines approximately a portion of a cylinder whose axis intersects the focal spot. The use of the partial cylindrical detector surface configuration equalizes the x-ray path from the tube to each row of detector elements.

In another embodiment, the surface defined by the collective detector element faces approximates a portion of a sphere having its center located substantially coincident with the focal spot. The use of the spherical concave detector surface further improves upon the uniformity of detector response by locating every detector element substantially equi-distant from the x-ray tube focal spot.

In another embodiment, means is provided to scan the detector assembly relative to a subject located in the examination space, and the detector elements are adapted to respond to incident radiation to produce analog electrical charge signals indicative of the radiation. In such an embodiment, the imaging circuitry comprises time delay and integrate circuitry to shift and add the electrical charge signals along rows of detector elements in synchronism with detector scanning motion. The use of the time delay and integrate circuitry in this embodiment enhances the signal-to-noise ratio of data represented by the electrical charge signals, and improves the quality of the final image so produced from that data.

An important aspect of this invention is the incorporation of focused detector arrangements in medical imaging systems.

These and other advantages of the present invention will be appreciated by reference to the following detailed description, and to the drawings, in which:

BEST MODE OF CARRYING OUT THE INVENTION

Figure 1:
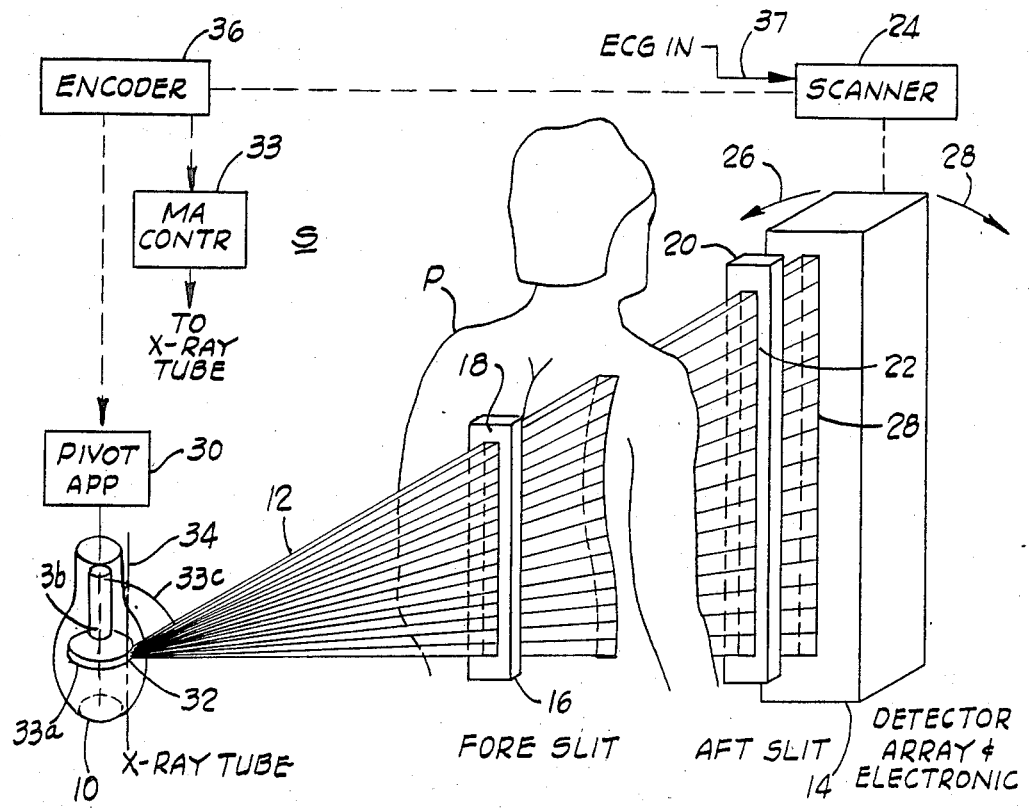
FIG. 1 is an isometric view of a medical diagnostic x-ray system incorporating the present invention.

A system S for performing digital scan projection radiography (SPR) is illustrated in general form in FIG. 1. The system S directs a pattern of x-rays through a patient P and produces, from information borne by the x-ray pattern emergent from the patient's body, a representation, generally in the form of a visible image, describing internal structure or condition of the patient's body.

The system S incorporates an x-ray source 10 for directing a beam of x-ray energy illustrated as a collection of rays 12 through the patient P and onto a detector assembly 14. A first collimator structure 16 defines a generally vertical fore slit 18 for collimating the x-rays emanating from the source into a spread beam lying generally within a vertical plane. A second collimator structure 20 defines an aft slit 22 located between the patient and the detector assembly, aligned with the fore slit and with the detector, for enhancing this collimation.

Mechanical structure (not shown) maintains a mutually constant relative alignment between the collimators 16, 20, the x-ray source 10 and the detector assembly 14.

In the preferred embodiment, mechanical means is provided for scanning the collimators and detector in unison relative to the patient's body in a manner described in more detail below.

The mechanical structure can suitably comprise a gantry structure of known configuration (not shown) which physically holds the collimators and detector in a rigid alignment, and mechanical drive means to move the entire gantry to effect scanning. Alternately, the components can be coupled to individual drive mechanisms and servo techniques can be employed in known fashion to maintain the desired alignment during scanning motion.

In the preferred embodiment, mechanical scanner apparatus 24 is coupled to the detector assembly 14 to move the detector along a generally arcuate path defined by the arrows 26, 28. The arcuate path is centered about a vertical axis 34 through a focal spot 32 of the tube 10, described in more detail below.

Pivoting apparatus 30 is coupled to the x-ray source. The apparatus 30 pivots the source, synchronously with detector and collimator arcuate motion, to continuously track the detector 14 and the mutually aligned collimators 16; 20.

The x-ray source 10 comprises an x-ray tube, and associated power circuitry (not shown) for electrically actuating the tube to produce x-rays (in pulsed or continuous mode) emanating from a focal spot 32 defined by the structure of the tube. Tube 10 produces x-rays by directing a stream of electrons onto an anode 33a of the tube, the anode rotating about an axis 33b. The pivoting motion effected by the pivot apparatus 30 causes the tube to pivot about the vertical axis 34 extending through the focal point 32.

the axis 33b of the rotatable anode 33a is, in the FIG. 1 embodiment, approximately parallel to the vertical axis 34 through the focal spot, the axis 34 being the axis of detector scanning as well, about which the arcuate detector path is centered.

In some instances, it is desirable to tilt the axis 33b slightly, with respect to the axis 34, by about 8 degrees, or a similar small amount.

This tilting optimizes the configuration of the pattern 12 of x-rays which emanate from the tube the propagate through the collimator slits 18, 22. More specifically, the tilt angle is chosen to maximize the uniformity of x-ray energy passing through all portions of the slits 18, 22. The tilting is desirable for uniformity maximization because the x-ray energy produced by the tube 10 varies inherently with the angle 33c from the axis 33b at which energy emanates, and the degree of nonuniformity varies over the range of such angles. This is often called the "heel and toe effect" of the tube. The tilting angle is selected to enable the projection of energy through the slits 18, 22 from that range of angles 33c over which the x-rays are most uniform.

It is believed preferable to couple the detector assembly 14 to the master drive of the scanner apparatus and to control the tube and collimators to follow, since detector positioning is more critical than tube positioning.

An encoder 36 is coupled to the scanner apparatus 24 and produces a signal indicating the instantaneous position of the detector 14 along its arcuate path described by the arrows 26, 28. The output of the encoder 36 is directed to the pivot apparatus 30 for synchronizing the pivoting motion of the x-ray tube 10 with the arcuate motion of the detector 14 and collimators 16, 20, to maintain continuous alignment between the x-ray beam, collimators and detector assembly during scanning motion.

The scanner apparatus can be appropriately gated by a physiological signal, such as by an ECG signal 37, or by a signal indicating timing of administration of a contrast agent. Temporal subtraction studies can also be done, with sufficiently rapid retrace between scans.

An example of a type of encoder apparatus is described in U.S. Pat. No. 4,015,129, issued on Mar. 29, 1977 to Manring et al., incorporated expressly here by reference, and owned by the assignee of the present application.

The encoder 36 may also be coupled to a current control 33 of the x-ray tube 10. The encoder can adjust the tube current and hence, the intensity of x-ray output, as a function of the location of the detector along its scanning path. In the embodiment described here, the tube current can be controlled to decrease as a function of the degree of detector displacement from the center position along its scanning path. Thus, where the patient's body is less thick, i.e. near its right and left sides, x-ray output is reduced to maintain a more uniform x-ray flux at the detector throughout its scan.

The detector assembly 14 includes an array of individual detector elements, generally arranged within an elongated slot 28 defined by the detector assembly 14. The structure and arrangement of the detector elements is described in detail below. Each of the detector elements responds to light energy (generated by x-rays as described below) to produce an analog electrical charge signal which represents a characteristic of the x-ray which caused the production of the electrical signal.

In operation, the detector, collimators and x-ray tube are moved to the left as in the direction illustrated by the arrow 26 to prepare for a scan. In performing a scan, the x-ray tube 10 is actuated to produce x-ray energy. The scanner apparatus 24 and pivot apparatus 30 cooperate to synchronously scan the vertical spread beam of x-rays from left to right as shown in FIG. 1 across the patient's body. During this scanning motion, the detector elements of the detector assembly 14 produce the analog electrical signals.

Analog detector outputs from each of the detector elements are periodically sampled. Each sampling produces analog signals representing a portion of image information. Over the course of the scan from one side to the other side, signals are developed describing a plurality of image lines, which together constitute an area image of the patient's internal body structure.

The electrical signals are then digitized and processed to produce the desired patient imaging.

Figure 2:
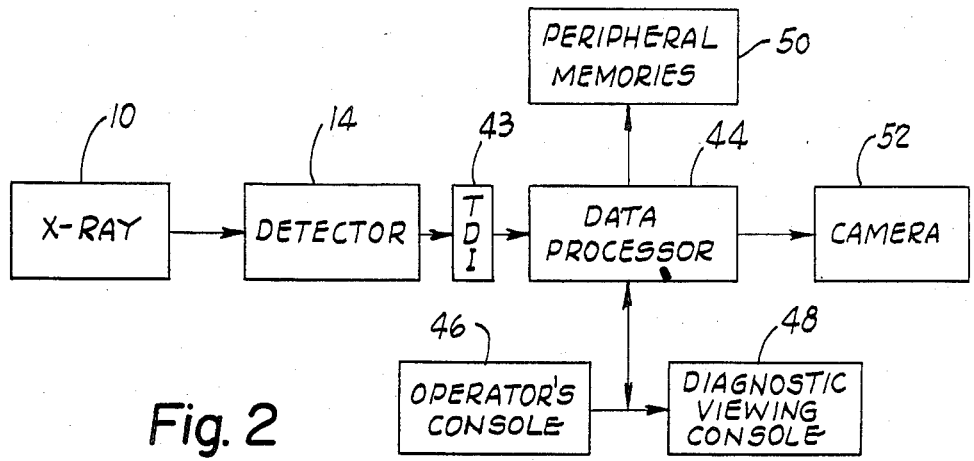
FIG. 2 is a block diagram illustrating components of the system of FIG. 1.

FIG. 2 illustrates a generalized block diagram of the system of FIG. 1. In FIG. 2, the x-ray source 10 directs x-rays to the detector assembly 14. The individual detector elements of the detector assembly 14 are mutually coupled to and associated with time delay and integrate (TDI) circuitry 43 which executes shift and add operations on the detector outputs in synchronism with detector scanning motion to produce an image indicating analog signals with enhanced signal-to-noise ratio. Signals from the detector 14 and TDI circuitry 43 are then transmitted to a data processor 44 which digitizes and processes the electrical signals. In response to commands from an operator's console 46, the data processor 44 produces various types of representations of internal body structure of the examined patient. In one mode, the data processor actuates a diagnostic viewing console 48 to produce directly a visible image of the patient's internal body structure which can be immediately employed by a radiologist for medical diagnostic purposes.

In another mode, the data processor 44 stores digital information representing patient image data in one or more peripheral memories 50. Optionally, a camera 52 can be coupled to the data processor.

Figure 3:
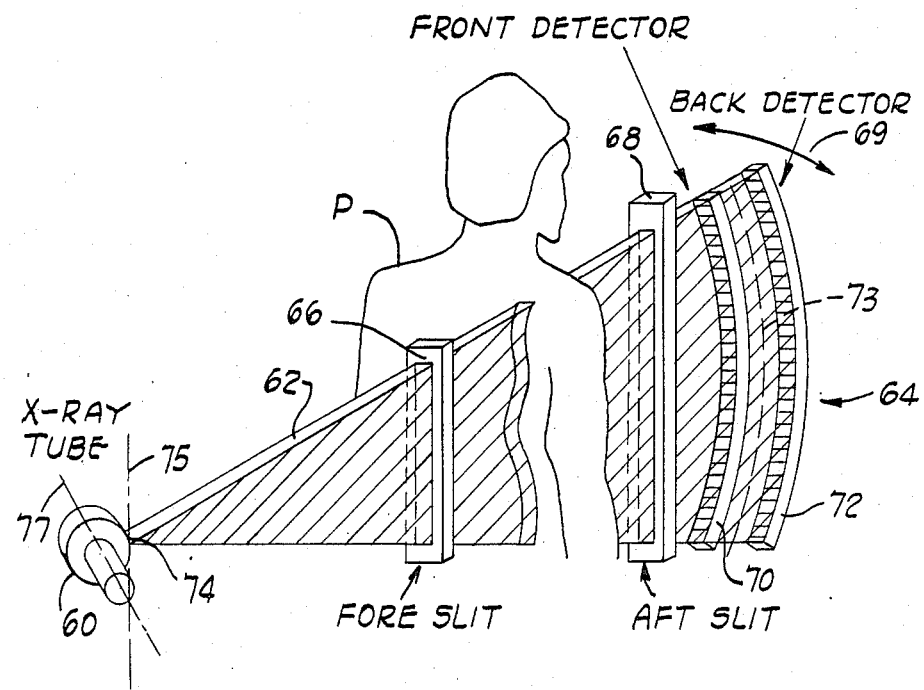
FIG. 3 is an isometric view illustrating detail of a portion of the system of FIG. 1.

FIG. 3 shows one embodiment of a focused detector. FIG. 3 illustrates an x-ray tube 60 directing a spread beam of x-rays 62 through a patient P toward the detector arrangement 64. Fore and aft collimators 66, 68 defining aligned collimator slits are also illustrated. The remainder of the system described above is omitted for simplicity and clarity.

The detector includes a first (front) array 70 of detector elements and a second (back) array 72 of detector elements located behind the first array with respect to the x-ray tube. Both the first and second arrays are aligned with the fore and aft slits. Radiation from the x-ray tube falls upon, and is partially absorbed by, the first array, and the remainder of the radiation, passing through the first array, falls upon and is detected by the second array. In this way, separate dual energy response is obtained, as explained in the Barnes published application incorporated above.

Each of the arrays includes a single line of detector elements arranged along an arcuate path defined by a portion of a circle having its center located at a focal spot 74 of the x-ray tube.

The detector arrays scan along arcuate paths concentric with the path indicated by the arrows 69. The concentric paths are centered about a vertical scanning axis 75 extending through the tube focal spot 74. The tube anode rotates about an axis shown at 77. The axis 77 is approximately perpendicular to the scanning axis 75.

This geometry reduces the nonuniformity of the x-ray energy across the beam set 62 propagating through the collimator 66, 68 by eliminating the effect of the "heel and toe effect" characteristic of the x-ray tube. According to the heel and toe effect, the x-ray energy from a tube varies as a function of the angle of x-ray emission with respect to the axis of anode rotation. Such radiation is far less a function of the angle of x-ray propagation taken radially with respect to the anode rotative axis.

In the FIG. 3 embodiment, the axis 77 is also tilted slightly from the perpendicular to the approximate plane defined by the aligned collimators 66, 68 and detector array layers 70, 72. The amount of tilting is about 8 degrees from the perpendicular to the plane so defined. The tilting is desirable for reasons analogous to those explained with respect to the tilting in FIG. 1.

Each detector element comprises a photodiode. Overlying each photodiode is a scintillation material responsive to x-rays to produce visible light energy.

Preferably, the scintillation material used in connection with the first array differs from that used in connection with the second array. The scintillation material associated with the first array is selected for its ability to absorb and produce light in response to x-rays from the source falling primarily within a relatively low energy range. The higher energy x-rays pass through the first array and fall on the second array, causing the scintillation material associated with the second array to produce light which is detected by the individual detector photodiodes of the second array. Suitable types, thicknesses and physical configurations of the scintillation material are defined in the above incorporated Barnes published European patent application.

The preferred detector embodiments of this invention described can suitably include a radiation filter, made of copper or brass sheet or other similar material, located at the region indicated by reference character 73, to "harden" the radiation energy reaching the second detector layer or array. Such filter elements are used to improve energy discrimination between the two detector layers in ways as are described in the above incorporated Barnes published European patent application.

The scintillation or phosphor material used in conjunction with the individual photodiode arrays discussed herein can suitably comprise a uniform single portion or layer of phosphor material overlying the entirety of the photodiode array without breaks or interruptions in its surface. Thus, the configuration of this embodiment forms a uniform smooth curved surface which comprises the energy receiving face of the detector array.

In another embodiment, each detector element photodiode can be provided with its own individual portion of scintillation phosphor material, rather than the entire array being covered with a single piece of such material. In this latter embodiment, the individual receiving faces of each of the detector elements, with their scintillators, collectively form a curved surface which is approximately smooth.

Known electronic and/or software correction means can be used to compensate, if need be, for any nonuniformity of transmission characteristics through the front detector array. This correction means can be associated with data processor 44.

Figure 4:
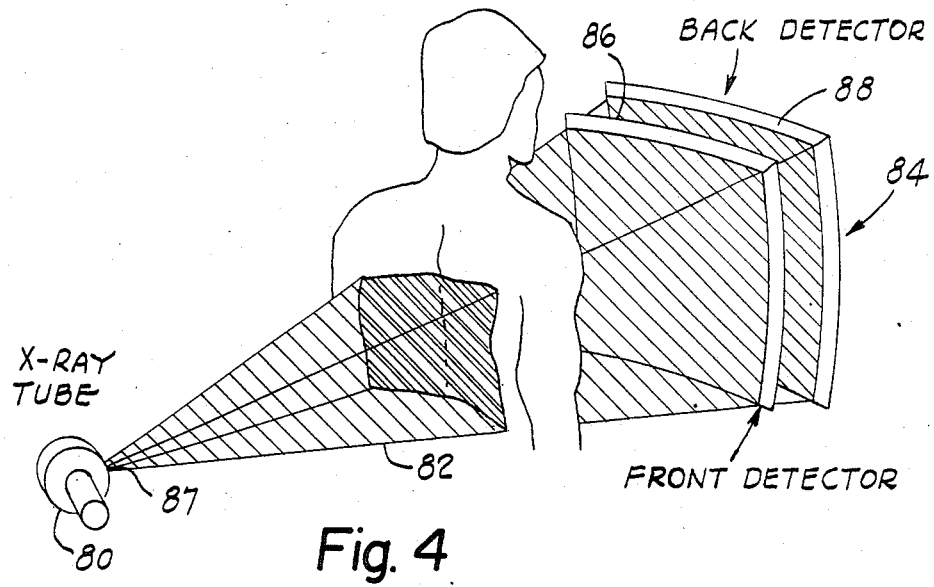
FIG. 4 is an isometric view illustrating detail of another embodiment of a portion of the system of FIG. 1.

FIG. 4 illustrates another embodiment of the invention in the form of an alternate detector array configuration. In FIG. 4, energy from an x-ray tube 80 is directed through a collimator (not shown) and in an area beam 82 through the patient, emerging therefrom to fall in a relatively large area of a detector assembly 84. In the embodiment of FIG. 4, a first detector array 86 includes a relatively large number of individual detector elements arranged in an area pattern, with the receiving surface of the first detector array collectively defining a portion of a sphere having its center at a focal spot 87 of the x-ray tube. The detector element arrangement (not shown) is as described in the above incorporated Kruger patent.

A second similar detector array 88 is located behind the first array with respect to the x-ray tube. The second array has a receiving surface defined by a portion of a sphere having a radius slightly larger than the sphere referred to in connection with the first array, and whose center is also located at the x-ray tube focal spot.

The source/detector arrangement shown in FIG. 4 incorporating the area beam can, but need not, be scanned. That is, the area beam can be directed constantly or in pulsed mode to pass simultaneously through a predetermined relatively large area of the patient's body, or the beam and detector can be scanned in unison, analogous to the manner of scanning described in connection with FIG. 1.

An alternative embodiment employs the spherically or cylindrically configured, detector arrays of FIG. 4 and in FIGS. 5-7 (described below) in conjunction with the thin spread beam and collimator arrangement as illustrated in FIG. 3. In this alternate embodiment, the spread beam is scanned across the area detector, the detector remaining stationary relative to the patient.

Techniques for processing image data from non-scanned detector arrays, or single line scanned arrays in scanned multi-linear arrays is discussed below.

Figure 6:
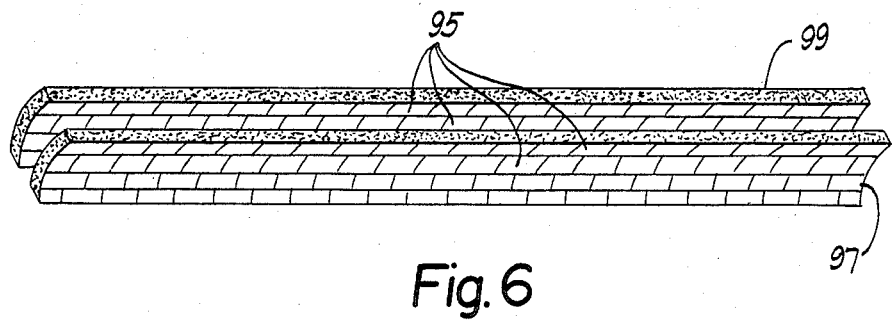
FIGS. 5 and 6 are isometric views showing detail of portions of two further embodiments of a portion of the system illustrated in FIG. 1.
Figure 5:
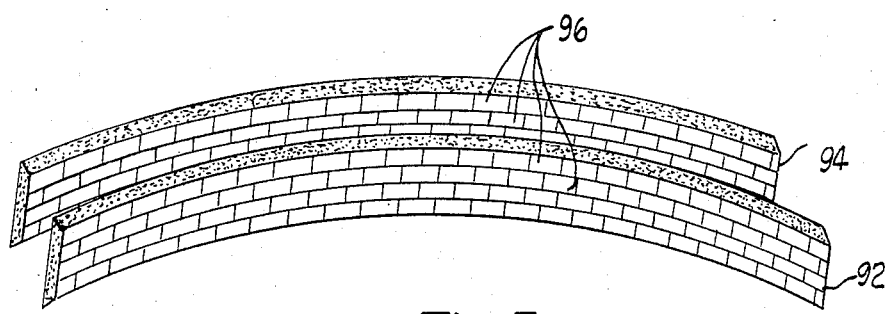

Other embodiments of focused detector configurations are illustrated in FIGS. 5 and 6. FIG. 5 shows a portion of each of two stacked detector arrays 92, 94. The detector of FIG. 5 comprises a multiplicity of detector elements 96 whose receiving surfaces collectively define approximately a portion of a cylinder having a horizontal axis intersecting the focal spot of the x-ray tube. Either a single layer, or a dual layer, or "stacked" detector, as shown, can be used.

FIG. 6 illustrates another embodiment, wherein the detector element receiving faces 95 define collectively a portion of a cylinder having a vertical axis through the x-ray tube focal spot. A dual layer (97, 99) arrangement is shown, but a single layer can be used if desired.

It is important to note that in the detector arrangements of FIGS. 4-7, (FIG. 7 to be discussed below) known time delay and integration (TDI) circuitry can be employed, where the beam and detector are synchronously scanned, to enhance the signal-to-noise ratio of information derived from the scanned detector. In the embodiment of FIG. 4, for example, a rectangular array of detector elements can be used. When such an array is used, the techniques for employing TDI output signal enhancement are described in the above incorporated Kruger patent. The embodiments of FIGS. 5-7 can also incorporate rectangular arrays of elements and TDI.

Figure 7:
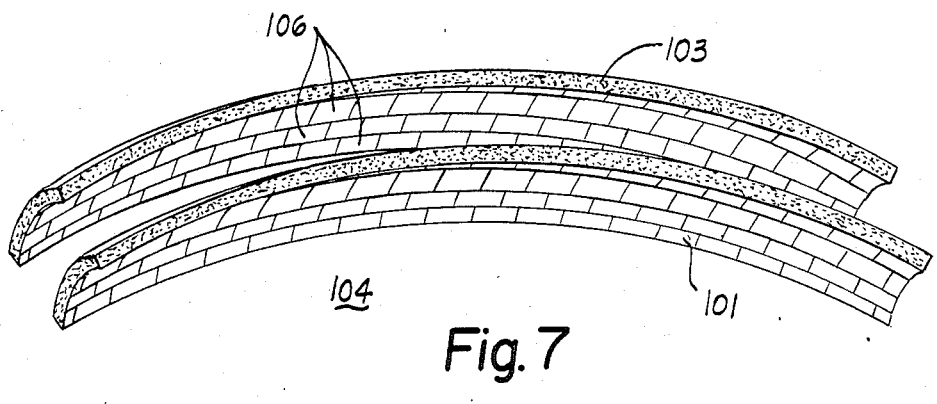
FIG. 7 is an isometric view illustrating detail of a portion of the system as shown in FIG. 4.
Figure 8:
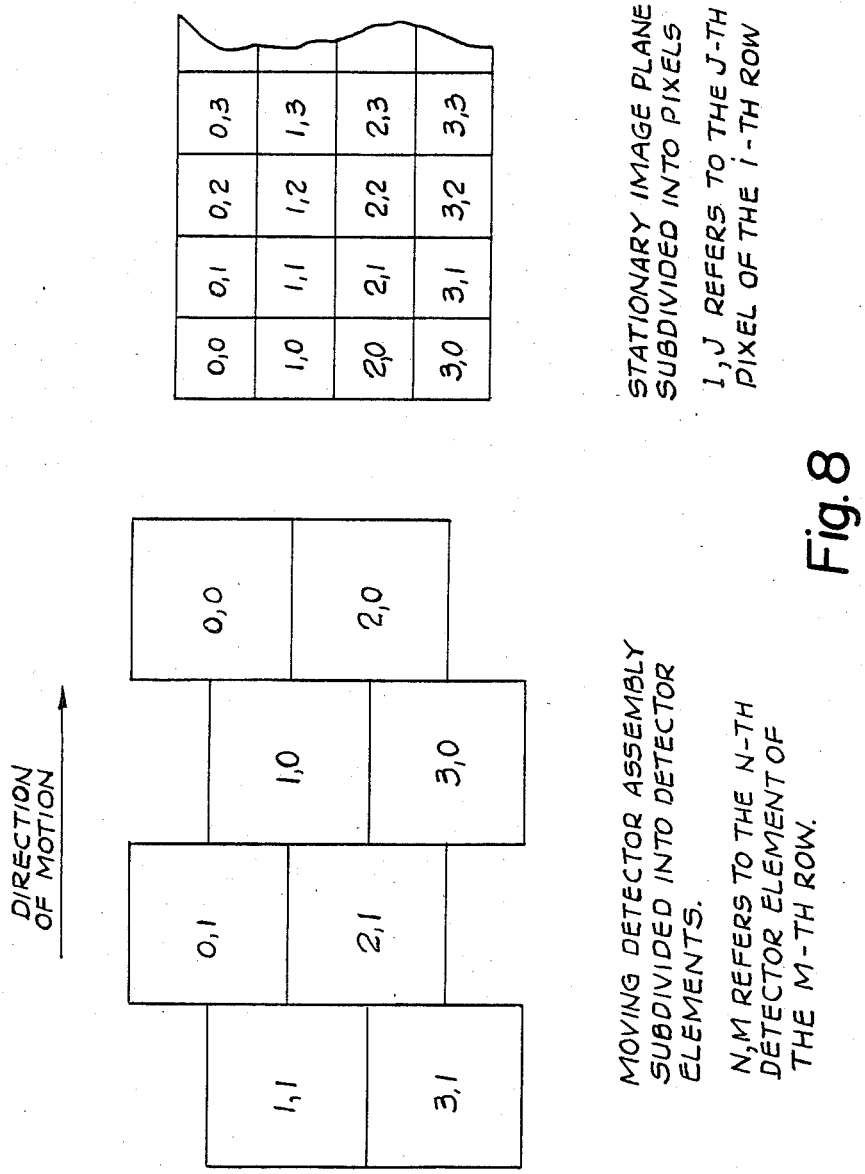
FIG. 8 is a graphical representation of a principle of operation of system embodiments shown in FIGS. 5-7.

A further aspect of this invention is illustrated in FIGS. 5-7. FIG. 7, for example, depicts a portion of a double layer (101, 103) spherical (three dimensionally curved) detector assembly 104, similar to that of FIG. 4, but wherein individual detector elements 106 are arranged in a staggered fashion. FIGS. 5 and 6 illustrate embodiments wherein the detector elements are arranged in staggered patterns and collectively define a portion of a cylinder.

In the embodiments of FIGS. 5–7, incorporating staggered arrays of detector elements, time delay and integrate (TDI) signal enhancement techniques can also be employed. Apparatus and circuitry for implementing TDI principles to processing of information from staggered detector arrays are set forth in detail in the above incorporated Sones et al. applciation.

Each column (extending substantially vertically in FIGS. 5–7) is offset vertically from its adjacent columns by a distance equal to one half the center-to-center spacing between adjacent elements along a column.

It should be understood that, while the preferred embodiments described herein are intended to include a dual layered stacked detector, the invention also encompasses embodiments similar to those of the Figures, but employing only single layer focused detectors.

Similarly, the embodiments described herein could include more than two stacked detector layers used analogously to those described here.

Also, it should be understood that each of the embodiments of FIGS. 4–7 preferably include a beam hardening filter analogous to the filter 73 shown in FIG. 3, and the x-ray tube geometry described in connection with FIGS. 1 and 3.

While the descriptions of embodiments of this invention have discussed primarily the use of curved arrays of individual detector elements, the invention is not limited to such arrays. The invention also encompasses the use of curved portions of x-ray film, and curved portions of storage phosphor material responsive to x-rays.

It is to be understood that the foregoing description of the present invention is intended as illustrative, rather than exhaustive, of the invention. Those of ordinary skill in the relevant art may be able to make certain additions, deletions of modifications to the subject matter described above, without departing from the spirit or the scope of this invention, as defined in the appended claims.

What is claimed is:

1. A focused radiation detector comprising:
   (a) a rear curved area detector layer, and
   (b) a front curved area detector layer having a curvature similar to that of said rear detector layer and being superposed with respect to said rear layer.

2. A slit projection digital radiography system for imaging penetrating electromagnetic radiation, said system comprising:
   (a) a radiation source including means for producing a thin spread beam of radiation generally defining a plane;
   (b) a radiation detector forming at least one unclosed curved concave surface whose curvature defines a first axis, with said concave surface disposed toward the source and containing penetrative radiation-sensitive material, said detector comprising:
      (i) a first detector layer for detecting radiation of predominantly a first energy range, and
      (ii) a second detector layer positioned behind said first layer, relative to the source, for detecting radiation of a second energy range, and
   (c) means for scanning said detector along a path defining an axis parallel to said plane and orthogonal to said first axis.

3. A slit scanning projection digital radiography imaging system comprising:
   (a) a radiation source;
   (b) a curved dual energy radiation detector disposed toward said source said curvature defining a first axis;
   (c) mounting structure for maintaining a spacing between said source and detector,
   (d) power means for actuating said source, and
   (e) means for scanning said detector about an axis perpendicular to said first axis.

4. The system of claim 3, wherein:
   (a) said source comprises an x-ray tube, and
   (b) said detector comprises:
      (i) a first x-ray sensitive layer for detecting x-ray energy of predominantly a first range, and
      (ii) a second x-ray sensitive layer overlying said first layer for detecting x-ray energy of predominantly a second range.

5. The system of claim 3, wherein:
   (a) said source defines a focal spot of radiation emanation, and
   (b) said detector surface defines an arc having its center substantially coincident with said focal spot.

6. The system of claim 3, wherein said detector comprises:
   a plurality of individual detector elements.

7. The system of claim 6, wherein:
   (a) said detector elements are each responsive to incident radiation to produce an electrical signal indicating said radiation, and
   (b) said system further comprises circuitry coupled to said detector elements and responsive to said electrical signals to produce a representation of a radiation pattern when incident on said elements.

8. A medical diagnostic slit scan projection digital radiography system comprising:
   (a) an x-ray source including means for producing a thin fan beam of radiation for projection through a subject;
   (b) a dual energy x-ray detector comprising a curved array of detector elements and additional detector elements superimposed over said array;
   (c) structure for supporting said source and detector in a mutually facing relationship;
   (d) means for rotationally moving said fan beam and detector relative to a subject to maintain alignment therebetween, said movement having a component in a direction orthogonal to the plane defined by the fan beam;
   (e) power circuitry for actuating said source to propagate x-ray energy toward said detector, and
   (f) imaging means coupled to said detector for producing a representation of x-ray energy projected on the detector.

9. The system of claim 8, wherein:
   (a) said detector curved array defines substantially an arc, and
   (b) said source comprises an x-ray tube having a focal spot substantially coincident with the center defined by said arc.

10. The system of claim 8, wherein said detector comprises:
    a multi-layered multiple energy detector apparatus.

11. The system of claim 8, wherein:
    (a) said detector defines a concave face disposed toward said source, said face defining a portion of a sphere, and
    (b) said source comprises an x-ray tube having a focal spot substantially coincident with the center of said sphere.

12. A digital slit scan projection radiography system for imaging separate patterns of penetrative radiation falling respectively within first and second energy ranges, said system comprising:
 (a) a penetrative radiation source defining a focal spot from which radiation primarily emanates for producing a fan beam of radiation defining a plane and rotating said beam about a first axis in said plane;
 (b) a detector assembly comprising:
  (i) a first array of detector elements mounted with each element having a receiving portion facing said source and said receiving portions of said first element array being each maintained at substantially a first predetermined distance from said focal spot, and
  (ii) a second array of detector elements each having a radiation receiving portion, said radiation receiving portions of each of said second array of elements being maintained at a second predetermined distance from said focal spot, one of said first and second arrays being superposed over the other with respect to radiation when emanating from the focal spot;
 (c) power means for actuating the source to propagate radiation from said focal spot toward said detector arrays,
 (d) means for moving said detector along a curved path defining a second axis parallel to said first axis;
 (e) circuitry coupled to said detector elements for producing by energy subtraction presentations of energy incident on said first and second arrays.

13. The system of claim 12, wherein:
each detector element of one of said detector arrays is aligned with a corresponding detector element of the other of said arrays along a line extending from said focal spot.

14. The system of claim 12, wherein each of said first and second arrays comprises a curvilinear array of detector elements.

15. A system for separately imaging shadowgraphic patterns of projected penetrative radiation falling within first and second energy ranges, said system comprising:
 (a) a penetrative radiation source defining a focal region from which radiation is primarily emitted when the source is actuated;
 (b) a first curved multi-element, multilinear portion containing a first penetrative radiation sensitive material disposed such that each point defined by the surface of said portion is located at substantially a same first predetermined distance from said focal region;
 (c) a second curved multi-element, multilinear portion containing a second penetrative radiation sensitive material, each point defined by the surfaces of said second portion being located at substantially a same second predetermined distance from said focal region, said second distance differing from said first distance.

16. The system of claim 15, further comprising:
means for producing separate images by separately utilizing the radiation energy response of said first and second curved portions.

17. The system of claim 15, wherein:
one of said first and second portions being superposed over the other, such that radiation directed toward one of said layers is at least partially intercepted by the other.

18. The system of claim 15, wherein:
each of said curved portions defines a portion of a sphere.

19. The system of claim 15, wherein said radiation source comprises an x-ray tube the x-ray energy from which is emitted substantially from a neighborhood about a focal spot.

20. A medical diagnostic x-ray system comprising:
 (a) a radiation source assembly for propagating penetrative radiation outwardly in a pattern definable by a solid angle;
 (b) multi-element, multilinear area detector assembly having radiation sensitive material defining at least one face for receiving radiation from said source, said receiving face disposed to receive energy from said source substantially normally to said surface at substantially all locations of said detector face subtended by said solid angle and for producing analog electrical signals corresponding to received radiation, and
 (c) means for producing an indication of a pattern of radiation energy incident upon said detector.

21. A medical diagnostic system comprising:
 (a) a source of penetrative radiation;
 (b) a detector unit comprising at least a $3 \times 3$ array of individual detector elements each having a radiation receiving face, said elements being positioned so that the element receiving faces collectively define a substantially curved surface disposed toward the source, and said detector elements being arranged in a staggered pattern, and
 (c) means coupled to said detector elements for producing a representation of a pattern of radiation from said source incident on detector unit.

22. In a radiation imaging system including a radiation source and imaging circuitry integratable with a detector for producing an image representing radiation incident on the detector, the improvement comprising:
a focused radiation detector comprising:
 (a) a rear curved multi-element cellular area detector layer, and
 (b) a front area detector layer superposed with respect to said rear layer to intercept radiation from the source prior to interception of source radiation by said rear detector layer.

23. In a slit scan projection energy subtraction digital x-ray imaging system including an x-ray source and imaging circuitry coupleable to a detector for producing an image of radiation incident on the detector, the improvement comprising:
a split energy x-ray detector apparatus comprising:
 (a) a first detector structure comprising a first x-ray sensitive material arranged to define a first curved concave face, and
 (b) a second detector structure comprising a second x-ray sensitive material arranged to define a second face overlying said first layer structure.

24. In a system for imaging penetrating electromagnetic radiation, including a radiation source, the improvement comprising:
a radiation detector curved to form a dome shaped concave surface disposed toward the source and containing penetration radiation-sensitive material.

25. A digital radiography system comprising:
 (a) a multi-element multilinear curved detector assembly including a plurality of individual detector elements each having radiation sensitive material defining a face, said element faces collectively defining generally a concave curved surface;
(b) an x-ray tube having a focal spot from which said tube primarily propagates x-ray energy, said tube being sufficiently displaced from said detector assembly to define a subject examination space;
(c) power means for actuating a tube to propagate x-ray energy toward the detector assembly;
(d) imaging circuitry at least partially integral with said detector assembly, and
(e) display apparatus coupled to said imaging circuitry for producing an image of a subject located in said examination space.

26. A slit scan projection digital radiography x-ray imaging system comprising:
(a) an x-ray detector;
(b) an x-ray tube spaced from said detector to provide a subject examination space therebetween, said tube comprising an anode mounted for rotation about and axis and means for directing an electron beam incident upon said anode;
(c) power means for actuating said tube to propagate x-rays through said examination space toward said detector;
(d) apparatus for scanning said detector along a substantially arcuate path centered about a scanning axis, and
(e) apparatus for maintaining said tube with said anode rotational axis approximately perpendicular to said scanning axis.

27. The system of claim 26, wherein said tube maintaining apparatus maintains said tube positioned with said anode rotational axis tilted from said perpendicular by approximately eight degrees.

28. A system for imaging penetrative electromagnetic radiation, said system comprising:
(a) a radiation source:
(b) a radiation detector forming a domed shape and having a curved concave surface disposed toward the source and containing penetrative radiation sensitive material, and
(c) imaging circuitry coupled to said detector.

29. A system for imaging penetrative electromagnetic radiation, said system comprising:
(a) a radiation source;
(b) a radiation detector forming an unclosed curved concave surface disposed toward said source and including penetrative radiation sensitive material, said detector including a first detector portion comprising a multiplicity of individual detector elements including a first material for detecting radiation of predominantly a first energy range, and a second detector portion comprising a plurality of individual detector elements positioned behind said first material, relative to the source, of a second material for detecting radiation of a second energy range, said detector elements each producing an electrical signal in response to detection of radiation by said materials, and
(c) energy subtraction means coupled to said detector for providing an image of a shadowgraphic pattern of radiation projected incident upon said detector.

30. An x-ray imaging system comprising:
(a) an X-radiation source defining a focal spot;
(b) a detector assembly comprising sets of discrete radiation detectors, each set comprising a plurality of discrete detector elements, said detector element sets defining, in a plane extending through both detector sets, a cross section including at least two concentric arcs, said concentric arcs each having a center located substantially coincident with the focal spot of said x-ray source, and
(c) means, integral to said detector elements, for producing an image of a shadowgraphic pattern of x-radiation incident upon said detector assembly.

31. A medical diagnostic slit scan projection digital radiography system comprising:
(a) an x-ray source including means for producing a thin fan beam of radiation for projecting through a subject, said source comprising an x-ray tube having a focal spot;
(b) a curved multi-layered multiple energy detector apparatus comprising a curved array of detector elements and additional detector elements arranged behind said curved array with respect to said source;
(c) structure for supporting said source and detector in a substantially facing relationship;
(d) means for rotationally moving said fan beam and detector relative to a subject to maintain alignment therebetween, said movement having a component in a direction orthogonal to the plane defined by the fan beam;
(e) power circuitry for actuating said source to propagate x-ray energy toward said detector, and
(f) imaging means coupled to said detector for producing a representation of x-ray energy projected on the detector.

32. The system of claim 31, wherein:
said detector curved array defines substantially an arc having a center of curvature substantially coincident with said focal spot.

33. A digital slit scan projection radiography system for imaging separate patterns of penetrative radiation falling respectively within first and second energy ranges, said system comprising:
(a) a penetrative radiation source defining a focal spot from which radiation primarily emanates for producing a fan beam of radiation defining a plane and rotating said beam about a first axis in said plane;
(b) a detector assembly comprising:
(i) a first array of detector elements defining a dome shaped portion of a sphere and being mounted with each element having a receiving portion facing said source and said receiving portions of said first element array being each maintained at substantially a first predetermined distance from said focal spot, and
(ii) a second array of detector elements each having a radiation receiving portion, said second array defining a dome shaped portion of a sphere, said radiation receiving portions of each of said second array of elements being maintained at a second predetermined distance from said focal spot, one of said first and second arrays being superposed over the other with respect to radiation when emanating from said focal spot;
(c) power means for actuating the source to propagate radiation from said focal spot toward said detector arrays,
(d) means for moving said detector along a curved path defining a second axis parallel to said first axis;
(e) circuitry coupled to said detector elements for producing separate representations of energy incident on said first and second arrays.

34. A medical diagnostic slit scan projection energy subtraction digital radiography system comprising:
(a) an x-ray source including apparatus cooperative with said source for producing a thin fan beam of radiation for projection through a subject, said x-ray source defining a focal spot from which x-ray energy primarily emanates;
(b) a dual energy x-ray detector assembly comprising:
  (i) a first curved array of x-ray detector elements defining a first radius of curvature and being focused substantially on said focal spot;
  (ii) a second curved array of detector elements defining a second radius of curvature greater than said first radius of curvature, said second curved array also being substantially focused on said focal spot;
(c) structure for supporting said source and detector assembly;
(d) means for rotationally moving said fan beam and detector assembly relative to a subject to maintain alignment therebetween, said movement having a component in a direction orthogonal to the plane defined by the fan beam;
(e) power circuitry to actuating said source to propagate x-ray energy toward said detector, and
(f) imaging means coupled to said first and second curved detector element arrays for performing energy subtraction by the use of information produced by said detector arrays respectively, and for producing a visual representation of x-ray energy projected onto the detector assembly.

35. A medical diagnostic slit scan projection energy subtraction digital radiography system comprising:
(a) an x-ray source including apparatus cooperative with the source for producing a thin fan beam of radiation for projection through a subject;
(b) a dual energy x-ray detector comprising two stacked layers of detector elements one behind the other with respect to the source;
(c) structure for supporting said source and detector assembly in a mutually facing relationship;
(d) means for moving said fan beam and detector assembly relative to a subject to maintain alignment therebetween;
(e) power circuitry for actuating said source to propagate x-ray energy toward said detector, and
(f) imaging means coupled to said respective detector array layers for performing energy subtraction on information derived from said respective detector layers and for producing a representation of x-ray energy projected on the detector.

* * * * *